US006967108B1

(12) United States Patent
Endl et al.

(10) Patent No.: US 6,967,108 B1
(45) Date of Patent: Nov. 22, 2005

(54) HUMAN MONOCLONAL ANTIBODIES TO THE ISLET CELL ANTIGEN IA-2

(75) Inventors: Josef Endl, Weilheim (DE); Thomas Wild, Penzberg (DE); Suzanne Elisabeth Berlo, Haaren (NL); Verena Litty, Munich (DE)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 09/786,040

(22) PCT Filed: Aug. 27, 1999

(86) PCT No.: PCT/EP99/06321

§ 371 (c)(1),
(2), (4) Date: Jul. 17, 2001

(87) PCT Pub. No.: WO00/12558

PCT Pub. Date: Mar. 9, 2000

(30) Foreign Application Priority Data

Sep. 1, 1998 (DE) .......................................... 198 39 736

(51) Int. Cl.[7] .............................................. G01N 33/53
(52) U.S. Cl. ........................ 436/547; 436/548; 530/380; 530/388.1; 530/388.15; 530/861; 530/866; 530/868
(58) Field of Search ................................ 436/547, 548; 530/380, 388, 388.15, 861, 866, 868, 388.1

(56) References Cited

U.S. PATENT DOCUMENTS

| | | | |
|---|---|---|---|
| 5,200,318 A | 4/1993 | Rabin et al. ................ | 435/7.21 |
| 5,888,813 A | 3/1999 | Endl et al. ................... | 435/338 |

OTHER PUBLICATIONS

Ackermann et al., Biotechnology and Bioengineering. vol. 45, pp. 97–106, 1995.*
Kohler., Science. vol. 233 pp. 1281–1286. 1986.*
Steinunn Baekkeskov, et al., "Identification of the 64K Autoantigen in Insulin–Dependent Diabetes as the GABA–Synthesizing Enzyme Glutamic Acid Decarboxylase" Nature, vol. 347, Sep. 13, 1990 (p. 151–156).
Julia Dittler, et al., "GADIA2–Combi Determination as First–Line Screening for Improved Prediction of Type 1 Diabetes in Relatives" Diabetes, vol. 47, Apr. 1998 (4pgs).
Peter Ifversen, et al., "Effect of Cell–Derived Growth Factors and Cytokins on the Clonal Outgrowth of EBV–Infected B Cells and Established Lymphoblastoid Cell Lines" Hum. Antibod. Hybridomas, 1993, vol. 4, Jul. (pp. 115–123).

Anne–Marie Madec, et al., "Four IgG Anti–Islet Human Monoclonal Antibodies Isolated from a Type 1 Diabetes Patient Recognize Distinct Epitopes of Glutamic Acid Decarboxylase 65 and Are Somatically Mutated" GAD65–Driven Somatic Selection in an IDDM Patient (pp. 3541–3549).

Ahuva Nissim et al., "Antibody Fragments from a 'Single Pot' Phage Display Library as Immunochemical Reagents" The EMBO Journal vol. 13, No. 3, pp. 692–698, 1994.

Jerry P. Palmer, et al., "Insulin Antibodies in Insulin–Dependent Diabetics Before Insulin Treatment", Science, vol. 222 (3pgs).

Mark A. Payton, et al., Realtionship of the 37,000– and 40,000–M, Tryptic Fragments of Islet Antigens in Insulin–Dependent Diabetes to the Protein Tyrosine Phosphatase–Like Molecule IA–2 (ICA512), Tyrosine Phospatases as Autoantigens in Type 1 Diabetes, (pp. 1506–1511).

Eric Peyron, et al., Human Monoclonal Autoantibodies Specific for the Bullous Pemphigoid Antigen 1 (BPAg1)1, The Journal of Immunology, 1994 (pp. 1333–1339).

Massimo Pietropaolo, et al., "Islet Cell Autoantigen 69 kD (ICA69)" Molecular Cloning and Characterization of a Novel Diabetes–Associated Autoantigen J. Clin. Invest. The American Society for Clinical Investigation, Inc., vol. 92, Jul. 1993, 359–371.

U. Roll, et al., "Combined Antibody Screening for Improved Prediction of IDDM– Modern Strategies" Exp. Clin. Endocrinol Diabetes 105 (1997) 1–14.

Michael Solimena, et al., "ICA 512, An Autoantigen of Type 1 Diabetes, Is An Intrinsic Membrane Protein of Neurosecretory Granules" The EMBO Journal vol. 15, No. 9, pp. 2102–2114, 1996.

Baowei Zhang, et al., "Autoantibodies to IA–2 in IDDM" Location of Major Antigenic Determinants, Diabetes, vol. 46, Jan. 1997 (pp. 40–43).

* cited by examiner

Primary Examiner—Bao-Thuy L. Nguyen
(74) Attorney, Agent, or Firm—McDonnell Boehnen Hulbert & Berghoff LLP

(57) ABSTRACT

The invention concerns human monoclonal antibodies to the islet cell antigen IA-2, a process for their production, the use of human monoclonal antibodies in a method for detecting antibodies to IA-2, a method for detecting antibodies to the islet cell antigen IA-2 and a method for detecting the islet cell antigen IA-2 in a sample.

3 Claims, No Drawings

SEQUENCE LISTING

<160> NUMBER OF SEQ ID NOS: 2

<210> SEQ ID NO 1
<211> LENGTH: 24
<212> TYPE: DNA
<213> ORGANISM: Unknown
<220> FEATURE:
<223> OTHER INFORMATION: Primer

<400> SEQUENCE: 1

-continued

```
atgcagcaag acaacgagcg cctg                                          24
```

<210> SEQ ID NO 2
<211> LENGTH: 21
<212> TYPE: DNA
<213> ORGANISM: Unknown
<220> FEATURE:
<223> OTHER INFORMATION: Primer

<400> SEQUENCE: 2

```
tcactggggc agggccttga g                                             21
```

HUMAN MONOCLONAL ANTIBODIES TO THE ISLET CELL ANTIGEN IA-2

The invention concerns human monoclonal antibodies to the islet cell antigen IA-2, a process for their production, the use of human monoclonal antibodies in a method for detecting antibodies to IA-2, a method for detecting antibodies to the islet cell antigen IA-2 and a method for detecting IA-2.

Type I insulin-dependent diabetes mellitus (IDDM) is due to an autoimmune destruction of the insulin-producing β cells of the pancreas. The development of autoantibodies to β cell antigens precedes the development of a clinically diagnosable diabetes. These autoantibodies are sensitive markers for identifying the preclinical phase of the disease. Antibodies that react with the β cells in the islets of Langerhans are also frequently found in newly diagnosed diabetic patients. The autoantibodies as a whole are also referred to as islet cell antibodies (ICA).

ICA are sensitive and specific markers for the prognosis and diagnosis of human IDDM. Previously characterized islet cell antigens to which autoantibodies are formed include insulin (Palmer et al. 1983, Science 222, 1337–1339), glutamate decarboxylase (GAD, Bakkeskov et al. 1990, Nature 347, 151–156), carboxypeptidase H (Castano et al. 1991, J. Clin. Endocrinol. Metab. 73, 1197–1201) islet cell antigen ICA 69 (Pietropaolo et al. 1993, J. Clin. Invest. 92, 359–371) and the antigen IA-2 which is also referred to as ICA512 (Solimena et al. 1996, EMBO Up to now it has not been possible to clarify whether autoantibodies that are directed towards β cell antigens contribute directly to the development of the disease or whether the occurrence of the autoantibodies is a phenomenon that occurs after the destruction of the β cells.

However, according to present knowledge the occurrence of autoantibodies correlates with the development of diabetes.

It has been shown that especially autoantibodies to IA-2 occur in most of the newly diagnosed IDDM patients and that the IA-2-specific autoantibodies are associated with a rapid progression of the diabetes disease. In addition IA-2-specific autoantibodies appear to be more specific for IDDM than GAD autoantibodies and moreover occur less frequently in other autoimmune diseases without IDDM (Roll and Ziegler 1997, Exp. Clin. Endocrinol. Diabetes 105, 1–14).

The autoantigen IA-2 is a transmembrane protein that has a segment that crosses the membrane and a cytoplasmic domain (IA-2ic) which contains the epitopes for antibody binding (Solimena et al. 1996, EMBO J. 15, 2102–2114). IA-2 is an intrinsic membrane protein of secretory vesicles that is expressed in peptide secreting endocrine cells and in neurones which contain neurosecretory vesicles. IA-2 has a significant homology to IA-2β which is also known as phogrin. IA-2β is a transmembrane protein like IA-2, but unlike IA-2 it is primarily expressed in β cells. IA-2β and IA-2 are proteins of the receptor type and both belong to the class of protein tyrosine phosphatases (Roll and Ziegler 1997, supra).

In the prior art ICA (islet cell antibodies) are determined for the detection of IDDM by measurements on pancreatic tissue sections using indirect immunofluorescence. In this method the autoantibodies in the sample to be examined that bind to the islet cell structures are detected by fluorescent-labelled antibodies that are specific for human IgG. However, these ICA measurements are technically very complicated and difficult to standardize since the results obtained with different pancreatic tissues from different donors varies greatly.

In the prior art autoantibodies to IA-2 and GAD are also determined by simple radioligand binding assays in serum samples. These assays use in vitro translated, radioactively labelled antigens (Dittler, J. et al 1998, Diabetes 47, 592–597). In order to prepare radioactively labelled antigens, the cDNA of the respective antigen is transcribed in vitro using a rabbit reticulocyte lysate. The mRNA is then translated in the presence of radioactively labelled amino acids (usually labelled with $^{35}$S, sulphur-35). Binding of the autoantibodies to the labelled antigen is detected by means of the radioactive signal of the labelled antigen after separation of the antigen-antibody complex from the free antigen by for example filtration or solid phase binding.

Although these detection methods can be partially automated, they have the major disadvantage that one has to work with radioactivity which requires laborious and expensive precautionary measures. The labelling efficiencies for the antigen that can be achieved by in vitro translation vary greatly from batch to batch. In addition the labelled antigens have a very short shelf life due to radiolysis and the short half-life of sulphur-35.

A diagnostic test for the direct detection of IA-2-specific autoantibodies that can be carried out simply, rapidly and in an automated manner has previously not been described in the prior art. This is in particular due to the fact that standardized IA-2-specific auto-antibodies have previously not been available. Hitherto only high-titre sera from IDDM patients were used as a standard or calibration material. The disadvantage of this material is that such serum is not available in an unlimited amount and thus batch and patient-dependent variations in the antibody content of the respective standard sera occur. Hence there is no comparability between experimental results from different laboratories.

The object was therefore to provide human monoclonal antibodies which specifically recognize the islet cell antigen IA-2 and to provide a diagnostic test procedure for the quantitative detection of the IA-2-specific autoantibodies by means of a standard curve which at least partially overcomes the disadvantages of the prior art.

The object is achieved by human monoclonal antibodies which specifically react with islet cell antigen IA-2. These for example include the antibodies which are produced by the cell line IA-2, 96-3-1, deposited at the DSMZ ("Deutsche Sammlung von Mikroorganismen und Zellkulturen GmbH", Braunschweig, Germany) on 13.08.1998 under the number DSM ACC2365.

The invention therefore concerns human monoclonal antibodies to the islet cell antigen IA-2. These antibodies are preferably of the IgG isotype, particularly preferably of the IgG1 isotype.

It is known in the prior art that human autoantibodies can be produced against the islet cell antigen GAD (glutamate decarboxylase) (EP-A-0 499 176). The described method comprises the following steps: Immortalizing human lymphocytes of prediabetics or diabetics, treating the culture supernatant of the immortalized cells (by EBV transformation) with a conjugate of antibodies to human Fcγ and a label, subsequent treatment with human immunoglobulin, incubation with immobilized human pancreatic islet cells or immobilized GAD, identification of an immortalized human cell culture which produces an antibody to pancreatic islet cells by determining the label bound to the immobilized islet cells or to the immobilized GAD, isolation of a human immortalized cell which produces this antibody, proliferation of this immortalized cell and isolation of the monoclonal antibody produced by these cells.

However, the method described in EP-A-0 499 176 does not allow the production of human monoclonal antibodies to IA-2. The first difficulty already becomes apparent in the selection of the donor lymphocytes. It is not possible to use any donor lymphocytes, but rather the lymphocytes must be derived from selective prediabetics or diabetics with high IA-2-specific serum antibody titres.

The antibody titres are determined by a radioligand binding assay. In this assay the DNA coding for IA-2 is transcribed in vitro by a reticulocyte lysate and translated in the presence of $^{35}$S-methionine. Subsequently a few microlitres (2–5 µl have proven to be suitable) patient serum is incubated with the radioactively labelled IA-2 and the immune complexes are separated from free antigen over protein-A Sepharose. The radioactivity bound to the protein-A Sepharose is determined in a scintillation counter. The measured cpm are converted into arbitrary units by means of a selected high titre patient serum. For example it was defined that 1000 cpm corresponds to 100 U in the patient serum used in this study. This patient serum is used as an arbitrary standard for the determinations. Only lymphocytes whose donors had a titre of more than 80 U were used for the transformations since IA-2-positive primary cultures were only discovered for these donors.

Moreover it proved to be advantageous to carry out a preselection for IgG-producing B lymphocytes. In peripheral blood there are ca. 10 times more IgM-producing B lymphocytes than IgG-producing B cells. On the other hand the relevant autoantibodies to IA-2 are of the IgG subtype (Zhang et al, 1997, Diabetes 46, 40–43). The relevant B cell subpopulation can be enriched 10-fold by isolating the membrane IgG-positive B lymphocytes. These are isolated by labelling the human B lymphocytes with an antibody from the mouse that is specific for human IgG and subsequently binding magnetic beads that are coated with sheep anti-mouse IgG. The labelled cells can be positively selected from the cell suspension by applying a magnet.

Furthermore problems occurred in the culture of the immortalized lymphocytes since the immortalized IA-2-specific B cells only had a low proliferation rate and were frequently overgrown by unspecific but rapidly growing immortalized B cells. It turned out that the proliferation of the immortalized IA-2-specific B cell lines can be greatly improved by adding growth factors such as IL-6 or IL-10. An additional problem was that the immortalized B cell lines secrete factors which adversely affect the growth of the cell lines. These factors include above all TGF-beta, IF-gamma and TNF-alpha. Removal of these inhibitory factors by frequently changing the culture medium results in a higher transformation rate and a more rapid growth of the EBV-transformed B cell lines.

A crucial factor for successful cloning (see below) of the resulting EBV-transformed B lymphocytes is to introduce limiting amounts of B lymphocytes into the individual wells (wells of the microtitre plate) right from the beginning. The prior art recommends several thousand purified peripheral mononuclear cells per well (Peyron, E. et al. 1994, J. Immunology 153, 1333–1339; Madec. A.-M. et al 1996, J. Immunology 156, 3541–3549). It surprisingly turned out that no more than 400 IgG-positive cells/well can be used for the primary transformation. The transformation rate is about 1 out of 80 B cells, i.e. a maximum of 5 different clones grow per well. This increases the probability that one can isolate the relevant clones in the subsequent single cell cloning in which only a few EBV-transformed B cell clones grow (often only 1–2%). It is also surprising that most of the positive primary wells can be isolated at an even lower seeding density which can be interpreted to mean that already too many clones are formed with 400 B cells per well and consequently clones that grow more slowly are suppressed by rapidly growing cells.

After a growth period of ca. 2 weeks the culture supernatants of the primary cell cultures are then tested for the production of IA-2-specific antibodies for example by means of an ELISA test on immobilized IA-2. Screening for IA-2-specific antibodies by means of the cytoplasmic domain of IA-2 which is also referred to as IA-2ic has proven to be particularly suitable according to the invention.

So-called feeder cells have to be added in the subsequent single cell cloning for the stabilization of the cell lines since EBV-transformed B cell lines cannot survive at a low cell density (<25 per well). Autologous (derived from the same donor) or allogenic (derived from a different donor) peripheral blood lymphocytes irradiated with 4000 rad are used as feeder cells.

The cloning efficiency can be decisively improved by removing cytotoxic T lymphocytes (CD8-positive cells) from the feeder cell population. The CD8 cells are preferably removed by immunomagnetic separation. For this the peripheral blood lymphocytes are for example incubated with magnetic microbeads to which monoclonal antibodies to the human CD8 antigen are coupled. The labelled cells are removed by applying a magnet, the remaining cells are irradiated and used at a concentration of 20,000–50,000 per well.

It has also proven to be advantageous for the production of the antibodies according to the invention to carry out a quality check of the feeder cells. It was found that the growth-promoting function of these feeder cells varies greatly from donor to donor. The feeder cells of some donors even had an inhibitory effect on growth. Hence a major improvement was to firstly examine each new batch of feeder cells on an established monoclonal EBHV-transformed B cell line (MICA 5) as a test cell line for their suitability for the cloning procedure and to sort out "harmful" feeder batches. For this purpose single cell clonings of MICA 5 were carried out on irradiated blood lymphocytes from different donors. The cloning efficiency was determined after ca. 3 weeks by microscopic determination of the number of growth wells. Only those feeder cells were used which enabled a cloning efficiency of at least 20%.

The immortalization step can be carried out by transformation with EBV (Epstein Barr virus) known to a person skilled in the art. This transformation is preferred according to the invention. The most frequently described method in the literature for EBV transformation (see Ifversen, P. et al 1993, Hum. Antibod. Hybridomas 4, 115–123) is to incubate B lymphocytes with EBV for 2–3 hours to allow virus uptake. Afterwards the cells are washed to remove the virus. However, it was surprisingly found that the transformation rate could be increased by not washing out the virus but instead to incubate it together with the B cells during the entire incubation period up to the first change of medium (after ca. 7 days).

However, the immortalization can also be carried out by fusion with suitable myeloma cells. It is also conceivable that the monoclonal antibodies to IA-2 according to the invention could be produced by the so-called phage display method (Nissim, A. et al 1994, EMBO J. 13, 3, 692–698). In this method the mRNA is isolated directly from the lymphocytes of the IDDM patients. The immunoglobulin genes can be amplified (for example by means of the polymerase chain reaction) from the cDNA prepared in this manner. The genes produced in this manner can in turn be expressed in a phage library as Fab or single chain Fv from which the phages binding to IA-2 can be isolated.

It was not possible to produce human monoclonal antibodies to the islet cell antigen IA-2 until the difficulties described above had been overcome.

Hence a preferred subject matter of the invention are monoclonal antibodies that bind to IA-2 and which are produced by the cell line IA-2, 96-3-1, deposited on 13.08.1998 at the DSMZ ("Deutsche Sammlung von Mikroorganismen und Zellkulturen GmbH", Mascheroder Weg 1b, D-38124 Braunschweig, Germany) under the number DSM ACC2365. The cell line DSM ACC2365 is also a subject matter of the invention.

Antibodies are also a subject matter of the invention which can bind to IA-2 in an equivalent manner to those produced by the cell line IA-2, 96-3-1 (DSM ACC2365). The term "can bind in an equivalent manner" refers to antibodies in which there is a detectable epitope overlap with the defined known antibody. This epitope overlap can be easily detected with the aid of a competitive test system. For example an enzyme immunoassay is used to examine the extent to which an antibody competes with the known antibody for binding to a defined antigen or to a defined epitope (for example IA-2ic). For this immobilized IA-2ic antigen is for example incubated with the known monoclonal antibody which carries a label and with an excess of the antibody under examination. It can then be easily determined to what extent the examined antibody can displace the defined antibody from binding to the antigen by detection of the bound label. If there is a displacement of at least 50% with a $10^5$-fold excess, then an epitope overlap is present.

The invention additionally concerns human monoclonal antibodies to the islet cell antigen IA-2 which can be obtained by the process steps of immortalizing human lymphocytes from prediabetics or diabetics with high serum antibody titres (>80 U) to IA-2, culturing the immortalized lymphocytes with growth factors while simultaneously removing inhibitory factors by frequently changing the medium, detecting the IA-2-specific human monoclonal antibodies in the culture supernatant preferably by means of ELISA, cloning the human immortalized cell line which produces this antibody in the presence of feeder cells which contain no cytotoxic T lymphocytes, proliferating this immortalized cell optionally with the addition of growth factors, and isolating the monoclonal antibody produced by this clone.

The invention also concerns a process for the production of human monoclonal antibodies which specifically react with the islet cell antigen IA-2 comprising the steps immortalizing human lymphocytes from prediabetics or diabetics with high serum antibody titres (>80 U/ml) to IA-2, culturing the immortalized lymphocytes with growth factors while simultaneously removing inhibitory factors by frequently changing the medium, detecting the IA-2-specific human monoclonal antibodies in the culture supernatant preferably by means of ELISA, cloning the human immortalized cell line which produces this antibody in the presence of feeder cells which contain no cytotoxic T lymphocytes, proliferating this immortalized cell optionally with the addition of growth factors, and isolating the monoclonal antibody produced by this clone.

The individual steps of the process are carried out as described in the previous sections.

The term "monoclonal antibody" in the sense of the invention is understood to include all antibody fragments in addition to the intact immunoglobulins. These for example include Fab, Fab' or F(ab)'$_2$ fragments. If the term "antibody" is not supplemented by the words "monoclonal" or "polyclonal", then it means both types of antibodies i.e. chimeric constructs and all fragments listed above.

The IA-2-specific monoclonal antibodies according to the invention react specifically with IA-2 and they preferably react with the cytoplasmic part of IA-2 the so-called IA-2ic. Hence the invention also concerns antibodies to IA-2 which react specifically with the cytoplasmic part of IA-2 the so-called IA-2ic. The process steps described above are used analogously to produce these antibodies.

An ELISA test is preferably used to identify the IA-2-specific monoclonal antibodies. At least 1000 primary wells have to be tested for each donor in order to find anti-IA-2-specific EBV-transformed B cell lines. Such an extensive screening cannot be carried out with the very laborious RIA of the prior art. The very high sample throughput can only be achieved by developing an ELISA. This semiautomatic ELISA enables several thousand culture supernatants to be tested per day and hence allows the discovery of the very seldom event of an IA-2-positive primary well.

In the ELISA the streptavidin-coated microtitre plates are coated with IA-2-biotin or IA-2ic-biotin. Subsequently the coated plates are incubated with various dilution steps of human sera from prediabetics or established diabetics. Defined amounts of a purified human IA-2-specific antibody are incubated concurrently on the same microtitre plate. Afterwards the plates are washed and a peroxidase-labelled sheep anti-human-Fcγ-specific antibody conjugate is added to detect bound anti-IA-2 antibodies. Bound IA-2-specific antibodies are detected by a colour reaction with ABTS® (azino-di-[3-ethylbenzthiazoline sulfonate (6)], catalogue No. 756 407, Boehringer Mannheim GmbH Germany). The content of anti-IA-2 antibodies in patient sera can be deduced from the absorbances of the standard curve taking into consideration the dilution factor.

In order to prepare the antigen IA-2ic which is used in the ELISA, the IA-2ic gene was amplified from an islet cell-specific cDNA using the following primers which have been published by Payton et al. (1995) in J. Clin. Invest. 96, 1506–1511 : 5'-ATGCAGCAAGACAACGAGCGCCTG-3' and 5'-TCACTGGGGCAGGGCCTTGAG-3'

The amplification products were cloned into a pin point vector and expressed in E. coli as soluble, biotinylated fusion protein. The fusion protein was purified on monomeric avidin-Sepharose. The biotinylated IA-2ic was bound to streptavidin-coated microtitre plates, incubated with the IA-2-specific monoclonal antibodies according to the invention and bound antibody was detected by a peroxidase-labelled anti-human IqG conjugate. In order to exclude the possibility that the antibodies were directed against the biotinylated amino-terminal domain of the fusion protein, the biotin binding domain of the fusion protein (Tag protein) was also expressed alone and tested in the ELISA. The IA-2-specific antibodies did not recognize the Tag protein. The IA-2-specific antibodies were also tested in a RIA. For this the DNA for IA-2ic was transcribed and translated in vitro in the presence of $^{35}$S-methionine, incubated with the IA-2-specific antibodies and the immune complexes were immobilized by adding protein A Sepharose. The radioactivity in the immunoprecipitates was determined by liquid scintillation counting.

The present invention also includes a method for detecting human antibodies or autoantibodies to the islet cell antigen IA-2 in a sample. All formats familiar to a person skilled in the art come into consideration as test formats and an indirect ELISA test is preferred. It has proven to be suitable to contact purified native or recombinant IA-2 antigen or IA-2ic antigen with the sample such that the sample antibodies can bind specifically to the antigen. If the antigen is provided with a group that can bind to a solid phase such as biotin, then the immune complex can be subsequently immobilized on a streptavidin-coated solid phase. The antigen can also already be directly or indirectly bound to the solid phase when it is incubated with the sample. After separation of the solid from the liquid phase the sample antibodies are preferably detected by binding a labelled antibody which is directed against the Fc part of human antibodies, generally the Fc part of human IgG and subsequently measuring the label. All labels familiar to a person skilled in the art can be used as the label, for example enzymes such as peroxidase, haptens such as digoxigenin, fluorescent dyes or substances capable of electrochemiluminescence or chemiluminescence.

A competitive test format is also conceivable in which the IA-2 or IA-2ic antigen is bound directly or indirectly to a solid phase and a defined concentration of a labelled inventive human monoclonal antibody to IA-2 or IA-2ic is added as a receptor and incubated with the antigen. If the sample is added simultaneously or subsequently, the sample antibodies and labelled receptor antibodies compete with one another for binding to the antigen. After separating the solid from the liquid phase, the label is determined in one or both phases. A low signal of the label on the solid phase indicates a high concentration of sample antibodies.

Comparison of the resulting sample measurements with measured values for a series of standards that have been previously determined, enable quantification of the sample antibodies. Defined concentrations of the inventive monoclonal antibodies to IA-2 or IA-2ic are used in such a series of standards.

All body fluids familiar to a person skilled in the art can be used as samples for detecting antibodies to IA-2. These for example include whole blood, serum or plasma, urine and saliva.

A further subject matter of the invention is the use of a human monoclonal antibody to IA-2 or IA-2ic as a standard or as a receptor in a method for determining antibodies to an islet cell antigen, preferably to the islet cell antigen IA-2.

A further subject matter of the invention is the use of a human monoclonal antibody to the islet cell antigen IA-2 for isolating the islet cell antigen IA-2. In order to isolate the islet cell antigen IA-2, the inventive antibodies can be coupled to a solid phase by methods known to a person skilled in the art.

Subsequently the sample containing IA-2 is incubated with the antibodies bound to the solid phase and the other components are separated. Cleavage of the immune complex between the antibody and antigen for example by a high salt concentration and subsequent elution enable the antigen to be obtained in a pure form.

The invention also concerns anti-idiotypic antibodies whose antigen binding site corresponds to the structure of the antigen IA-2 or IA-2ic. Such an anti-idiotypic antibody can be obtained by immunization with a human antibody to IA-2 according to the invention, immortalizing the spleen cells of the immunized animals, cloning those immortalized cells which produce antibodies that bind to the binding region of the IA-2-specific antibodies and isolating the antibodies produced by these clones by known methods.

Another subject matter of the invention is a method for detecting IA-2 in a sample which is characterized in that at least one monoclonal antibody according to the invention is used for this as the binding partner. The test is preferably carried out as a sandwich ELISA. An antibody to IA-2 which can be an antibody according to the invention is used as a binding partner for this which is bound to a solid phase by methods known to a person skilled in the art (for example via biotin/streptavidin). The IA-2 present in the sample binds to the antibody that is bound to the solid phase. The bound IA-2 is detected by means of a further binding partner which carries a label. The further binding partner is also preferably an antibody and also binds specifically to IA-2 but recognizes a different epitope to that recognized by the binding partner that is bound to the solid phase. The labelled binding partner can be a monoclonal antibody according to the invention if the antibody bound to the solid phase recognizes another epitope. All labels familiar to a person skilled in the art can be used as the label. These for example include enzymes such as peroxidase, haptens such as digoxigenin, fluorescent dyes or substances capable of electro-chemiluminescence or chemiluminescence.

The invention is further elucidated by the following examples.

EXAMPLE 1

Selection of Donors for the Isolation of B Lymphocytes

In order to increase the probability of a successful transformation of anti-IA-2-specific B lymphocytes from peripheral blood, donors were selected for the lymphocyte isolation which had a high serum antibody titre against IA-2.

The antibodies were determined by an in vitro translation assay (see Zhang et al. 1997, Diabetes 46, 40–43 and Dittler J. et al 1998, Diabetes 47, 592–597). Blood was withdrawn from newly diagnosed diabetics and serum was obtained by known methods. A volume of 2–5 $\mu$l of the individual sera was incubated overnight at 4° C. with the IA-2ic polypeptide that was radioactively labelled (ca. 15,000 cpm) by in vitro translation in 50 $\mu$l precipitation buffer (20 mM Tris-HCl, pH 7.5, 150 mM NaCl, 1% Triton X-100, 0.1% aprotinin) while rotating. Subsequently 50 $\mu$l of a 50% protein A-Sepharose suspension was added and it was incubated for a further hour. Afterwards it was washed three times with the incubation buffer and the radioactivity of the beads was determined in a liquid scintillation instrument. A high titre diabetic serum which produced ca. 1000 cpm in the immunoprecipitate for a serum quantity of 5 $\mu$l was used as an arbitrary standard. This value was defined as being equivalent to 100 U. On this basis the normal sera had levels of ca. 5 U. Only lymphocytes from patients whose sera had a titre of more than 80 U were used for the subsequent transformation of the peripheral blood lymphocytes.

EXAMPLE 2

Cell Separation and EBV-transformation

Only those lymphocyte donors whose sera had a titre of at least 80 U were used to isolate B lymphocytes. 20–50 ml blood was collected from these donors and used to isolate the peripheral mononuclear cells (PBMNC) by means of density gradient centrifugation.

The classical tests for detecting IA-2-specific serum antibodies use protein A-Sepharose to separate the immune complexes. Hence it must be assumed that the anti-IA-2 antibodies are almost exclusively of the IgG immunoglobulin class (Zhang et al., Diabetes, 1997, 46, 40–43 and Dittler J. et al. Diabetes, 1998, 47, 592–597). However, since the B lymphocytes of peripheral blood produce predominantly IgM, the membrane IgG-positive B cells were isolated in order to enrich the relevant B cell subpopulation. For this the PBMNC were adjusted to a concentration of $3*10^6$ cells/ml with ice cold IMDM/10% foetal calf serum (IMDM/10% FCS). Subsequently an anti human-IgG antibody from the mouse was added at a concentration of 10 µg/ml. The cells were then rolled for 30 minutes at 4° C. to prevent the cells from sedimenting during the incubation. They were subsequently centrifuged at 200 * g for 10 minutes at room temperature, the supernatant was aspirated and the cells were washed twice with IMDM/l10% FCS.

Afterwards the cells were taken up in IMDM/10% FCS at a concentration of $1*10^7$ cells/ml (total cell count ca. $1*10^7$ cells) and incubated with Magnetobeads (Dynal M-280) which had been coated with sheep anti-mouse IgG.

Approximately 10 beads per target cell were added (it was assumed that about 5% of the PBMNC express membrane IgG).

The cells were rolled with the beads for 30 minutes at 4° C. Afterwards the reaction vessel was placed for 5 minutes in the magnetic holder in order to separate the labelled cells. The supernatant was aspirated, the beads were resuspended in 1 ml medium and again placed for 5 minutes in the magnetic holder. The supernatant was again aspirated, the tube was removed from the magnetic holder and the isolated cells were resuspended in 0.5 ml IMDM/10% FCS.

Subsequently 2 ml concentrated Epstein-Barr virus suspension was added. The virus suspension was obtained from the supernatant of a confluent culture of the B 95-8 marmoset cell line (ATCC CRL 1612). The B cells were incubated for 2 hours in an incubator at 3720 C., 7% $CO_2$ for the virus absorption. The tube was moved several times during the incubation phase in order to prevent cell sedimentation.

Afterwards a serial dilution of the separated B cells was made such that 100, 200 and 400 B cells were present in 100 µl IMDM/10% FCS. Then allogenic PBMNC (without CD8-positive cells) that had been irradiated with 4000 rad were added to these cell suspensions as feeder cells (50,000 feeder cells per 150 µl cell suspension). Subsequently 100 U/ml IL-6 was added. 150 µl cell suspension per well was aliquoted into 96-well round bottom plates and incubated for 2 weeks at 5% $CO_2$ and 37° C. The medium was changed after 7–10 days.

EXAMPLE 3

Screening Assay for EBV-transformed B Cell Lines that produce IA-2 antibodies

After 2 weeks the culture supernatants of the EBV lines were tested in an ELISA for reactivity to recombinant IA-2. The intracellular part of IA-2 (IA-2ic) was expressed as the antigen in *Escherichia coli* in combination with a biotin-labelled peptide at the $NH_2$ terminus. The fusion protein was purified by affinity chromatography on a streptavidin column.

Streptavidin coated microtitre plates were coated for one hour at room temperature with IA-2ic biotin at a concentration of 100 ng/ml. Subsequently the plates were washed with 0.15 mol/l NaCl/0.05% Tween 20. 50 µl RPMI/10% FCS was added first to the plates and subsequently 50 µl culture supernatant of the EBV-transformed B cells was added. It was incubated for 1 hour at room temperature while shaking. Afterwards the plates were washed and 100 µl of a peroxidase-labelled sheep anti-human Fcγ antibody (Boehringer Mannheim GmbH, catalogue No. 1089 196, 100 mU/ml in PBS/0.5% bovine serum albumin) was added to detect bound anti-IA-2 antibodies. Subsequently is was again incubated for 1 hour at room temperature while shaking. Excess conjugate was removed by washing three times with 0.15 mol/l NaCl/0.05% Tween 20. Subsequently 100 µl ABTS® (1 mg/ml, Boehringer Mannheim GmbH, catalogue No. 756 407) in 40 mmol/l citrate buffer pH 4.4 containing 3.25 mmol/l sodium perborate was added and the absorbance was measured at 405 nm after incubating for 45 minutes at room temperature while shaking.

In a typical transformation mixture $2-5*10^5$ membrane IgG-positive B cells were isolated from initially $1*10^7$ PBMNC. These were divided into ca. 1000 wells. The number of wells that were identified as positive in the screening test was in the range between 1 and 3 wells per 1000 tested wells. The absorbance of the positive wells was in the range 1500–2000 mA.

EXAMPLE 4

Cloning EBV-transformed B Cell Lines

Those EBV-transformed B cell lines whose culture supernatant reacted positive in the ELISA were cloned. For this the cells were deposited singly into 96-well microtitre plates with the aid of a fluorescence-activated cell sorter and irradiated CD8-depleted PBMNC ($5*10^4$ cells/well, 4000 rad) were added. The cloning medium was composed of IMDM/10% FCS/100 U/ml IL-6. The culture supernatants containing growing clones were tested by means of ELISA and the positive clones were expanded. Mass culture for isolating antibodies was carried out in a Tecno mouse bioreactor. The antibodies were isolated from the supernatant by ammonium sulfate precipitation and chromatography over protein A or protein G Sepharose.

---

What is claimed is:

1. A human monoclonal antibody that binds specifically to islet cell antigen IA-2 in a manner equivalent to that of an antibody from cell line IA-2, 96-3-1, deposit number DSM ACC2365.

2. The antibody of claim 1, wherein said antibody belongs to the immunoglobulin class IgG.

3. The antibody of claim 2, wherein said antibody belongs to the immnunoglobulin subclass IgG1.

* * * * *